US011426352B2

(12) United States Patent
Bussat et al.

(10) Patent No.: US 11,426,352 B2
(45) Date of Patent: *Aug. 30, 2022

(54) FREEZE-DRIED PRODUCT AND GAS-FILLED MICROVESICLES SUSPENSION

(71) Applicant: Bracco Suisse SA, Cadempino (CH)

(72) Inventors: Philippe Bussat, Pers-Jussy (FR); Anne Lassus, Veyrier (CH); Jean Brochot, Cruseilles (FR); Michel Schneider, Troinex (CH); Feng Yan, Grand Lancy (CH)

(73) Assignee: BRACCO SUISSE SA, Cadempino (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/611,034

(22) PCT Filed: May 14, 2020

(86) PCT No.: PCT/EP2020/063559
§ 371 (c)(1),
(2) Date: Nov. 12, 2021

(87) PCT Pub. No.: WO2020/229642
PCT Pub. Date: Nov. 19, 2020

(65) Prior Publication Data
US 2022/0202719 A1    Jun. 30, 2022

Related U.S. Application Data

(63) Continuation of application No. 16/788,083, filed on Feb. 11, 2020, now abandoned, which is a continuation-in-part of application No. 16/688,540, filed on Nov. 19, 2019, which is a continuation-in-part of application No. 16/413,526, filed on May 15, 2019, now abandoned.

(51) Int. Cl.
*A61K 9/19* (2006.01)
*A61K 9/127* (2006.01)
*A61K 49/22* (2006.01)

(52) U.S. Cl.
CPC .............. *A61K 9/19* (2013.01); *A61K 9/1271* (2013.01); *A61K 9/1277* (2013.01); *A61K 49/223* (2013.01)

(58) Field of Classification Search
None
See application file for complete search history.

(56) References Cited

U.S. PATENT DOCUMENTS

| 6,139,819 A | 10/2000 | Unger et al. |
|---|---|---|
| 8,293,214 B2 | 10/2012 | Swenson et al. |
| 9,364,569 B2 | 6/2016 | Schneider et al. |
| 9,789,210 B1 | 10/2017 | Robinson et al. |
| 10,588,988 B2 | 3/2020 | Robinson et al. |
| 2001/0008626 A1* | 7/2001 | Schneider ............ A61K 49/223 600/431 |
| 2006/0051297 A1* | 3/2006 | Schneider ............... A61P 43/00 424/9.52 |
| 2008/0063603 A1* | 3/2008 | Schneider ............ A61K 49/223 424/9.52 |
| 2010/0008978 A1 | 1/2010 | Drummond et al. |
| 2011/0200530 A1 | 8/2011 | Allemann et al. |
| 2011/0236320 A1 | 9/2011 | Schneider et al. |
| 2013/0101520 A1 | 4/2013 | Schneider et al. |
| 2018/0008731 A1 | 1/2018 | Bussat et al. |

FOREIGN PATENT DOCUMENTS

| CN | 102614125 A | 8/2012 | |
|---|---|---|---|
| EP | 1228770 A1 * | 8/2002 | ......... A61K 49/1806 |
| EP | 1228770 A1 | 8/2002 | |
| WO | 9409829 A1 | 5/1994 | |
| WO | 9818501 A2 | 5/1998 | |
| WO | 9955383 A2 | 11/1999 | |
| WO | 02055544 A2 | 7/2002 | |
| WO | 2003074005 A2 | 9/2003 | |
| WO | 03084574 A1 | 10/2003 | |
| WO | 2004069284 A2 | 8/2004 | |
| WO | 2007067979 A2 | 6/2007 | |
| WO | 2008075192 A2 | 6/2008 | |
| WO | 2010040772 A2 | 4/2010 | |
| WO | 2015192093 A1 | 12/2015 | |
| WO | 2016097130 A1 | 6/2016 | |
| WO | 2017117349 A2 | 7/2017 | |

OTHER PUBLICATIONS

International Search Report and Written Opinion for PCT/EP2020/063559, dated Aug. 6, 2020.
SP Scientific, "Basic principles of freeze drying," available at: https://www.spscientific.com/freeze-drying-lyophilization-basics/ (2017).
International Preliminary Report on Patentability for PCT/EP2020/063559, dated Sep. 7, 2021.

* cited by examiner

*Primary Examiner* — Isaac Shomer
(74) *Attorney, Agent, or Firm* — Vivicar Law, PLLC

(57) ABSTRACT

A method of manufacturing a suspension of gas-filled microvesicles by reconstituting a freeze-dried product and a suspension obtained according to said method, where the freeze-dried product has been subjected to a thermal treatment.

25 Claims, No Drawings

FREEZE-DRIED PRODUCT AND GAS-FILLED MICROVESICLES SUSPENSION

CROSS-REFERENCE TO RELATED APPLICATIONS

This application is the national stage application of corresponding international application number PCT/EP2020/063559, filed May 14, 2020, which is a continuation of U.S. application Ser. No. 16/788,083, filed Feb. 11, 2020, which is a continuation-in-part of U.S. application Ser. No. 16/688,540, filed Nov. 19, 2019, which is a continuation-in-part of U.S. application Ser. No. 16/413,526, filed May 15, 2019, which are hereby incorporated by reference in their entireties.

TECHNICAL FIELD

The invention relates to a new method of manufacturing a suspension of gas-filled microvesicles by reconstituting a freeze-dried product and to the suspension obtained according to said method.

BACKGROUND OF THE INVENTION

Rapid development of contrast agents in the recent years has generated a number of different compositions and formulations, which are useful in contrast-enhanced imaging of organs and tissues of human or animal body as well as in therapeutic treatments thereof.

A class of contrast agents particularly useful for Contrast Enhanced UltraSound imaging ("CEUS" imaging) includes suspensions of gas bubbles of nano- and/or micro-metric size dispersed in an aqueous medium. The gas is typically entrapped or encapsulated in a film-layer comprising, for instance, emulsifiers, oils, thickeners or sugars. These stabilized gas bubbles (dispersed in a suitable physiological solution) are generally referred to in the art with various terminologies, depending typically from the stabilizing material employed for their preparation; these terms include, for instance, "microspheres", "microbubbles", "microcapsules" or "microballoons", globally referred to here as "gas-filled microvesicles" (or "microvesicles").

UltraSound Contrast Agents ("USCAs") can be produced according to various manufacturing methods. One of these methods, see e.g. WO94/09829, entails the dissolution of an amphiphilic material (such as a phospholipid and/or fatty acid) and of a freeze-drying protecting compound (e.g. polyetheleneglycol) in an organic solvent; the obtained mixture is then subjected to freeze-drying, typically after being filled into vials, to remove the solvent and obtain a freeze-dried product. Another method, see e.g. WO2004/069284, entails the preparation of a microemulsion of water with a water immiscible organic solvent, said emulsion comprising an amphiphilic material and a freeze-drying protecting compound. The emulsion is then and subjected (upon distribution into vials) to a freeze-drying step to remove water and solvent.

The headspace of the vials, containing a freeze-dried solid product in powder form at the bottom thereof, is then filled with a suitable gas (e.g. a fluorinated gas) and finally sealed for storage. Before use, an aqueous suspension of microbubbles is easily prepared by introducing a suitable liquid into the vial (e.g. saline) and gently shaking the vial to dissolve the freeze-dried product.

A commercially available USCA which can be manufactured according to the above method is SonoVue® (or Lumason® in the USA), from Bracco.

The Applicant has now observed that the characteristics of a suspension of gas-filled microvesicles (particularly microbubbles) reconstituted from a freeze-dried product can be improved by introducing a final controlled thermal treatment (i.e. heating) at the end of the process for manufacturing the freeze-dried solid product.

SUMMARY OF THE INVENTION

According to an aspect, the invention relates to a method of manufacturing a freeze-dried composition suitable for the preparation of a suspension of stabilized gas-filled microvesicles, said composition comprising: (i) an amphiphilic material capable of stabilizing said gas microvesicles; and (ii) a freeze-drying protecting component; which comprises:
a. preparing a liquid mixture comprising said amphiphilic material and said freeze-drying protecting component in a solvent;
b. freeze-drying the liquid mixture to remove said solvent and obtain a freeze-dried product comprising said amphiphilic material and said freeze-drying protecting component; and
c. heating said freeze-dried product.

Preferably, said heating step comprises heating said product at a temperature higher than 35° C., more preferably at least 38° C. The heating temperature is preferably lower than 50° C., more preferably lower than 48° C.

In certain embodiments, the heating step is performed at ambient pressure.

Preferably, the heating step lasts for at least 8 hours, more preferably for at least 12 hours.

According to another aspect, the invention relates to a freeze-dried product obtained according to the manufacturing method described above.

According to another aspect, the invention relates to a suspension of gas-filled microvesicles obtained by reconstituting a freeze-dried product prepared according to the method of manufacturing described above, said suspension being obtained by admixing said product with a pharmaceutically acceptable liquid carrier in the presence of a physiologically acceptable gas under gentle agitation.

According to a further aspect the invention relates to method for manufacturing a suspension of gas-filled microvesicles stabilized by an amphiphilic material, which comprises:
a. preparing a freeze-dried product according to the manufacturing method illustrated above; and
b. reconstituting said product by admixing it with a pharmaceutically acceptable liquid carrier in the presence of a physiologically acceptable gas under gentle agitation, to obtain the suspension of gas-filled microvesicles.

DETAILED DESCRIPTION OF THE INVENTION

A suitable method for preparing injectable suspensions of gas-filled microvesicles comprises the reconstitution, in the presence of a suitable physiologically acceptable gas, of a freeze-dried product comprising an amphiphilic material capable of stabilizing said microvesicles (e.g. by forming a stabilizing layer at the liquid-gas interface) with an aqueous carrier.

The freeze-dried product is typically obtained by freeze-drying a liquid mixture comprising said amphiphilic material and a freeze-drying protecting component in a suitable solvent.

The liquid mixture which undergoes the freeze-drying process can be obtained according methods know in the art, disclosed e.g. in WO94/09829 or WO2004/069284.

Preparation of Liquid Mixture for Freeze-Drying

For instance, according to the process disclosed by WO94/09829, the amphiphilic material is dispersed into an organic solvent (e.g. tertiary butanol, dioxane, cyclohexanol, tetrachlorodifluoro ethylene or 2-methyl-2-butanol) together with a suitable freeze-drying protecting component. The dispersion containing the amphiphilic material and the freeze-drying protecting component is then subjected to freeze-drying to remove the organic solvent thus obtaining a freeze-dried product.

According to the alternative process disclosed in WO2004/069284, a composition comprising an amphiphilic material may be dispersed in an emulsion of water with a water immiscible organic solvent under agitation, preferably in admixture with a freeze-drying protecting component.

Suitable water immiscible organic solvents include, for instance, branched or linear alkanes, alkenes, cyclo-alkanes, aromatic hydrocarbons, alkyl ethers, ketones, halogenated hydrocarbons, perfluorinated hydrocarbons or mixtures thereof.

The emulsion may be obtained by submitting the aqueous medium and the solvent, in the presence of the amphiphilic material, to any appropriate emulsion-generating technique known in the art such as, for instance, sonication, shaking, high pressure homogenization, micromixing, membrane emulsification, high speed stirring or high shear mixing. The freeze-drying protecting component can be added either before or after the formation of the emulsion, e.g. as an aqueous solution comprising such freeze-drying protecting component. The so obtained microemulsion, which contains microdroplets of solvent surrounded and stabilized by the amphiphilic material, is then freeze-dried according to conventional techniques to obtain a freeze-dried material, which can then be used for preparing a suspension of gas-filled microvesicles.

Amphiphilic Material

According to a preferred embodiment, amphiphilic materials useful for preparing the above liquid mixtures comprise a phospholipid. Phospholipids, as other amphiphilic molecules, are generally capable of forming a stabilizing film of material (typically in the form of a mono-molecular layer) at the gas-water boundary interface in the final gas-filled microvesicles suspension, these materials are also referred to in the art as "film-forming" materials.

Phospholipids typically contain at least one phosphate group and at least one, preferably two, lipophilic long-chain hydrocarbon group.

Examples of suitable phospholipids include esters of glycerol with one or preferably two (equal or different) residues of fatty acids and with phosphoric acid, wherein the phosphoric acid residue is in turn bound to a hydrophilic group, such a, for instance, choline (phosphatidylcholines—PC), serine (phosphatidylserines—PS), glycerol (phosphatidylglycerols—PG), ethanolamine (phosphatidylethanolamines—PE), inositol (phosphatidylinositol). Esters of phospholipids with only one residue of fatty acid are generally referred to in the art as the "lyso" forms of the phospholipid or "lysophospholipids". Fatty acids residues present in the phospholipids are in general long chain aliphatic acids, typically containing from 12 to 24 carbon atoms, preferably from 14 to 22; the aliphatic chain may contain one or more unsaturations or is preferably completely saturated. Examples of suitable fatty acids included in the phospholipids are, for instance, lauric acid, myristic acid, palmitic acid, stearic acid, arachidic acid, behenic acid, oleic acid, linoleic acid, and linolenic acid. Preferably, saturated fatty acids such as myristic acid, palmitic acid, stearic acid and arachidic acid are employed.

Further examples of phospholipid are phosphatidic acids, i.e. the diesters of glycerol-phosphoric acid with fatty acids; sphingolipids such as sphingomyelins, i.e. those phosphatidylcholine analogs where the residue of glycerol diester with fatty acids is replaced by a ceramide chain; cardiolipins, i.e. the esters of 1,3-diphosphatidylglycerol with a fatty acid; glycolipids such as gangliosides GM1 (or GM2) or cerebrosides; glucolipids; sulfatides and glycosphingolipids.

As used herein, the term "phospholipid(s)" includes either naturally occurring, semisynthetic or synthetically prepared compounds that can be employed either singularly or as mixtures.

Examples of naturally occurring phospholipids are natural lecithins (phosphatidylcholine (PC) derivatives) such as, typically, soya bean or egg yolk lecithins.

Examples of semisynthetic phospholipids are the partially or fully hydrogenated derivatives of the naturally occurring lecithins. Preferred phospholipids are fatty acids di-esters of phosphatidylcholine, ethylphosphatidylcholine, phosphatidylglycerol, phosphatidic acid, phosphatidylethanolamine, phosphatidylserine, phosphatidylinositol or of sphingomyelin.

Examples of preferred phospholipids are, for instance, dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2 Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC), 1-palmitoyl-2-oleylphosphatidylcholine (POPC), 1-oleyl-2-palmitoyl-phosphatidylcholine (OPPC), dilauroyl-phosphatidylglycerol (DLPG) and its alkali metal salts, diarachidoylphosphatidyl-glycerol (DAPG) and its alkali metal salts, dimyristoylphosphatidylglycerol (DMPG) and its alkali metal salts, dipalmitoylphosphatidylglycerol (DPPG) and its alkali metal salts, distearoylphosphatidylglycerol (DSPG) and its alkali metal salts, dioleoyl-phosphatidylglycerol (DOPG) and its alkali metal salts, dimyristoyl phosphatidic acid (DMPA) and its alkali metal salts, dipalmitoyl phosphatidic acid (DPPA) and its alkali metal salts, distearoyl phosphatidic acid (DSPA), diarachidoylphosphatidic acid (DAPA) and its alkali metal salts, dimyristoyl-phosphatidylethanolamine (DMPE), dipalmitoylphosphatidylethanolamine (DPPE), distearoyl phosphatidyl-ethanolamine (DSPE), dioleylphosphatidyl-ethanolamine (DOPE), diarachidoylphosphatidyl-ethanolamine (DAPE), dilinoleylphosphatidylethanolamine (DLPE), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingomyelin (DSSP), dilauroyl-phosphatidylinositol (DLPI), diarachidoylphosphatidylinositol (DAPI), dimyristoylphosphatidylinositol (DMPI), dipalmitoylphosphatidylinositol (DPPI), distearoylphosphatidylinositol (DSPI), dioleoylphosphatidylinositol (DOPI).

Suitable phospholipids further include phospholipids modified by linking a hydrophilic polymer, such as polyethyleneglycol (PEG) or polypropyleneglycol (PPG), thereto. Preferred polymer-modified phospholipids include "pegylated phospholipids", i.e. phospholipids bound to a PEG polymer. Examples of pegylated phospholipids are pegylated phosphatidylethanolamines ("PE-PEGs" in brief) i.e. phosphatidylethanolamines where the hydrophilic ethanolamine moiety is linked to a PEG molecule of variable molecular weight (e.g. from 300 to 20000 daltons, preferably from 500 to 5000 daltons), such as DPPE-PEG (or DSPE-PEG, DMPE-PEG, DAPE-PEG or DOPE-PEG). For example, DPPE-PEG5000 refers to DPPE having attached thereto a PEG polymer having a mean average molecular weight of about 5000. An example of DPPE-PEG5000 is the methoxy terminated PEG derivative 1,2-dipalmitoyl-sn-glycero-3-phosphoethanolamine-N-[methoxy(polyethylene glycol)-5000].

In an embodiment the phospholipids may bear a reactive moiety which may then be reacted with a corresponding reactive moiety bearing a suitable active component (e.g. targeting ligand), in order to bind said active component to the microvesicle. Examples of suitable reactive moieties include, for instance, reactive groups capable of reacting with an amino group bound to an active component such as isothiocyanate groups (that will form a thiourea bond), reactive esters (to form an amide bond), aldehyde groups (for the formation of an imine bond to be reduced to an alkylamine bond); reactive groups capable of reacting with a thiol group bound to an active component, such as haloacetyl derivatives or maleimides (to form a thioether bond); reactive groups capable of reacting with a carboxylic group bound to an active component, such as amines or hydrazides (to form amide or alkylamide bonds). Preferably, the amphiphilic compound bearing the reactive moiety is a lipid bearing a hydrophilic polymer, such as those previously mentioned, preferably a pegylated phospholipid, e.g. DPPE-PEG2000, such as DPPE-PEG2000-maleimide.

Particularly preferred phospholipids are DAPC, DSPC, DPPC, DMPA, DPPA, DSPA, DMPG, DPPG, DSPG, DMPS, DPPS, DSPS and Ethyl-DSPC. Most preferred are DPPG, DPPS and DSPC.

Mixtures of phospholipids can also be used, such as, for instance, mixtures of DPPE and/or DSPE (including pegylated derivates), DPPC, DSPC and/or DAPC with DSPS, DPPS, DSPA, DPPA, DSPG, DPPG, Ethyl-DSPC and/or Ethyl-DPPC.

The phospholipids can conveniently be used in admixture with any other compound, preferably amphiphilic. For instance, lipids such as cholesterol, ergosterol, phytosterol, sitosterol, lanosterol, tocopherol, propyl gallate or ascorbyl palmitate, fatty acids such as myristic acid, palmitic acid, stearic acid, arachidic acid and derivatives thereof or butylated hydroxytoluene and/or other non-phospholipid (amphiphilic) compounds can optionally be added to one or more of the foregoing phospholipids, e.g. in proportions preferably below 50% by weight, more preferably up to 25% or lower. Particularly preferred as additional compound in admixture with phospholipids are fatty acids. Fatty acids useful in a composition according to the invention, which can be either saturated or unsaturated, comprise a $C_{10}$-$C_{24}$, aliphatic chain terminated by a carboxylic acid moiety, preferably a $C_{14}$-$C_{22}$ and more preferably a $C_{16}$-$C_{20}$ aliphatic chain. Examples of suitable saturated fatty acids include capric (n-decanoic), lauric (n-dodecanoic), myristic (n-tetradecanoic), palmitic (n-hexadecanoic), stearic (n-octadecanoic), arachidic (n-eicosanoic), behenic (n-docosanoic) and n-tetracosanoic acid. Preferred saturated fatty acids are myristic, palmitic, stearic and arachidic acid, more preferably palmitic acid. Examples of unsaturated fatty acids comprise myristoleic (cis-9-tetradecenoic), palmitoleic (cis-9-hexadecenoic), sapienic (cis-6-hexadecenoic), oleic (cis-9-octadecenoic), linoleic (cis-9,12-octadecadienoic), linolenic (cis-9,12,15-octadecatrienoic), gondoic (cis-11-eicosenoic), cis-11,14-eicosadienoic, cis-5,8,11-eicosatrienoic, cis-8,11,14-eicosatrienoic, cis-11,14,17-eicosatrienoic, arachidonic (cis-8,11,14,17-eicosatetraenoic) and erucic (cis-13-docosenoic) acid.

According to an embodiment, the mixture of amphiphilic materials comprises a mixture of DSPC, DPPG and palmitic acid.

According to an alternative embodiment, said amphiphilic material comprises a mixture of DSPC, DPPE-PEG5000 and palmitic acid, optionally further comprising a targeting ligand Targeting Ligands Compositions and microvesicles according to the invention may optionally comprise a targeting ligand.

The term "targeting ligand" includes within its meaning any compound, moiety or residue having, or being capable to promote, a targeting activity (e.g. including a selective binding) of the microvesicles of a composition of the invention towards any biological or pathological site within a living body. Targets with which targeting ligand may be associated include tissues such as, for instance, myocardial tissue (including myocardial cells and cardiomyocytes), membranous tissues (including endothelium and epithelium), laminae, connective tissue (including interstitial tissue) or tumors; blood clots; and receptors such as, for instance, cell-surface receptors for peptide hormones, neurotransmitters, antigens, complement fragments, and immunoglobulins and cytoplasmic receptors for steroid hormones.

The targeting ligand may be synthetic, semi-synthetic, or naturally-occurring. Materials or substances which may serve as targeting ligands include, for example, but are not limited to proteins, including antibodies, antibody fragments, receptor molecules, receptor binding molecules, glycoproteins and lectins; peptides, including oligopeptides and polypeptides; peptidomimetics; saccharides, including mono and polysaccharides; vitamins; steroids, steroid analogs, hormones, cofactors, bioactive agents and genetic material, including nucleosides, nucleotides and polynucleotides.

The targeting ligand may be a compound per se which is admixed with the other components of the microvesicle or may be a compound which is bound to an amphiphilic molecule (typically a phospholipid) employed for the formation of the microvesicle.

In one preferred embodiment, the targeting ligand may be bound to an amphiphilic molecule (e.g. a phospholipid) forming the stabilizing envelope of the microvesicle through a covalent bond. In such a case, the specific reactive moiety that needs to be present on the amphiphilic molecule will depend on the particular targeting ligand to be coupled thereto, as illustrated in detail above. In order to covalently bind a desired targeting ligand, at least part of the amphiphilic compound forming the microvesicle's envelope shall thus contain a suitable reactive moiety and the targeting ligand containing the complementary functionality will be linked thereto according to known techniques, e.g. by adding it to a dispersion comprising the amphiphilic components of the microvesicle. Preferably, the amphiphilic compound is a lipid bearing a hydrophilic polymer, such as those previously mentioned, preferably a pegylated phospholipid (e.g. DSPE-PEG2000). In this case, the targeting ligand is linked to a suitable reactive moiety on the hydrophilic polymer (e.g. DSPE-PEG2000-NH$_2$), optionally through a linker. The amphiphilic compound may be combined with the desired targeting ligand before preparing the microvesicle, and the so obtained combination may be used for the preparation of the microvesicle. Alternatively, the targeting ligand may be linked to the respective amphiphilic compound during the preparation of the microvesicle (e.g. in the intermediate microemulsion preparation of the process described in WO2004/069284). As a further alternative, the binding may take place on the formed microvesicle comprising an amphiphilic material bearing a reactive moiety.

According to an alternative embodiment, the targeting ligand may also be suitably associated with the microvesicle via physical and/or electrostatic interaction. As an example, a functional moiety having a high affinity and selectivity for a complementary moiety may be introduced into the amphiphilic molecule, while the complementary moiety will be linked to the targeting ligand. For instance, an avidin (or streptavidin) moiety (having high affinity for biotin) may be covalently linked to a phospholipid (or to a pegylated phospholipid) while the complementary biotin moiety may be incorporated into a suitable targeting ligand, e.g. a peptide or an antibody. The biotin-labelled targeting ligand will thus be associated with the avidin-labelled phospholipid of the microvesicle by means of the avidin-biotin coupling system. Alternatively, both the phospholipid and the targeting ligand may be provided with a biotin moiety and subsequently coupled to each other by means of avidin (which is a bifunctional component capable of bridging the two biotin moieties). Examples of biotin/avidin coupling of phospholipids and peptides are also disclosed in the above cited U.S. Pat. No. 6,139,819. Alternatively, van der Waal's interactions, electrostatic interactions and other association processes may associate with or bind to the targeting ligand to the amphiphilic molecules.

Alternatively, the phospholipid may be modified with a protein suitable for specific coupling to Fc domain of Immunoglubulin (Ig) such as Protein A, Protein G, Protein A/G or Protein L. According to an alternative embodiment, the targeting ligand may be a compound which is admixed with the components forming the microvesicle, to be eventually incorporated the microvesicle structure, such as, for instance, a lipopeptide as disclosed e.g. in International patent Applications WO 98/18501 or 99/55383.

Alternatively, a microvesicle may first be manufactured, which comprises a compound (lipid or polymer-modified lipid) having a suitable moiety capable of interacting with a corresponding complementary moiety of a targeting ligand; thereafter, the desired targeting ligand is added to the microvesicle suspension, to bind to the corresponding complementary moiety on the microvesicle.

Examples of suitable specific targets to which the microvesicles may be directed are, for instance, fibrin and the GPIIbIIIa binding receptor on activated platelets. Fibrin and platelets are in fact generally present in "thrombi", i.e. coagula which may form in the blood stream and cause a vascular obstruction. Suitable binding peptides are disclosed, for instance, in the above cited U.S. Pat. No. 6,139,819. Further binding peptides specific for fibrin-targeting are disclosed, for instance, in International patent application WO 02/055544.

Other examples of important targets include receptors in vulnerable plaques and tumor specific receptors, such as kinase domain region (KDR) and VEGF (vascular endothelial growth factor)/KDR complex. Binding peptides suitable for KDR or VEGF/KDR complex are disclosed, for instance, in International Patent application WO 03/74005, WO 03/084574 and WO2007/067979. In an embodiment, the targeting peptide is a dimeric peptide-phospholipid conjugate (lipopeptide) as described in WO2007/067979.

Freeze-Drying Protecting Component

As defined herein, a freeze-drying protecting component is a compound with cryoprotective and/or lyoprotective effect. Suitable freeze-drying protecting components include, for instance, carbohydrates, e.g. a mono- di- or poly-saccharide, such as sucrose, maltose, trehalose, glucose, lactose, galactose, raffinose, cyclodextrin, dextran, chitosan and its derivatives (e.g. carboxymethyl chitosan, trimethyl chitosan); polyols, e.g. sugar alcohols such as sorbitol, mannitol or xylitol; or hydrophilic polymers, e.g. polyoxyalkyleneglycol such as polyethylene glycol (e.g. PEG2000, PEG4000 or PEG8000) or polypropylenglycol. According to an embodiment said freeze-drying protecting component is polyethylene glycol, preferably PEG4000. PEG4000 as used herein has its normal meaning in the field, indicating a polyethyleneglycol having a molecular weight of about 4000 g/mole, in general with a variation of +/−10% around said value.

Freeze-Drying Process

For the freeze-drying process, the liquid mixture containing the amphiphilic material and the freeze-drying protecting component (obtained e.g. according to either of the previously illustrated manufacturing processes), is typically sampled into glass vials (e.g. DIN8R or DIN20R) which are loaded into a freeze-dryer.

The freeze-drying process generally includes an initial step (primary drying) where the vials are rapidly deep-cooled (e.g. at temperatures of from −35° C. to −70° C.) to freeze the liquid(s) of the mixture and then subjected to vacuum (e.g. 0.1-0.8 mbar); during the primary drying, the substantial totality of the frozen liquid(s) (e.g. water and/or solvents) is removed by sublimation, typically up to about 95% of the total amount of liquid, preferably up to about 99%. After the primary drying, residual liquid (including possible interstitial water) can be further removed during the secondary drying, which is typically conducted at a temperature higher than room temperature, under vacuum (preferably by maintaining the same vacuum applied during the primary drying). The temperature during the secondary drying is preferably not higher than 35° C. The secondary drying can be stopped when the residual content of the liquid(s) reaches a desired minimum value, e.g. less 3% (preferably less than 1%) by weight of water with respect to the total mass of residual freeze-dried product, or e.g. less than 0.01% by weight, preferably less than 0.08%, for residual solvent(s).

After completion of the freeze-drying process (i.e. stopping of heating and vacuum removal), the freeze-dried product can undergo the additional thermal treatment step according to the invention, under ambient pressure. As used herein, the term "ambient pressure" refers to the normal value of atmospheric pressure values (i.e. about 103.12 kPa at sea level, typically between 95 and 104 kPa). Preferably the thermal treatment is performed on the sealed vial, after saturating the headspace of the vials containing the freeze-dried product with a suitable physiologically acceptable gas and then stoppering (e.g. with a rubber, such as butyl rubber, stopper) and sealing (e.g. with a metal, such as aluminium, crimp seal) the vials. In this case, the vials are preferably removed from the freeze-drier and introduced in a suitable oven for the thermal treatment. Alternatively, such thermal treatment can be performed on the open vial (which is preferably kept into the freeze-dryer), which is then saturated with the gas and then stoppered/sealed.

Examples of suitable physiologically acceptable gases include, for instance, fluorinated gases such as $SF_6$, $C_3F_8$, $C_4F_{10}$, optionally in admixture with air or nitrogen.

In an embodiment, the gas $SF_6$ is used in combination with a mixture of amphiphilic materials comprising DSPC, DPPG and palmitic acid, as above defined.

In another embodiment, the gas $C_4F_{10}$, or a mixture of $C_4F_{10}$ with nitrogen, is used in combination with a mixture of amphiphilic materials comprising DSPC, DPPE-PEG5000 and palmitic acid, optionally further comprising a targeting ligand, as above defined Other Components Other components, e.g. excipients or additives, may either be present in the dry formulation for the preparation of the microvesicles or may be added together with the aqueous carrier used for the reconstitution thereof, without necessarily being involved (or only partially involved) in the formation of the stabilizing envelope of the microvesicle. These include for instance pH regulators, osmolality adjusters, viscosity enhancers, emulsifiers, bulking agents, etc. and may be used in conventional amounts.

Suspension of Gas-Filled Microvesicles

The suspension of gas-filled microvesicles can then be prepared by reconstituting the freeze-dried product with a physiologically acceptable (aqueous) carrier, under gentle agitation. Suitable physiologically acceptable (aqueous) carriers include, for instance, water for injection, saline or glucose solution, optionally containing excipients or additives as illustrated above.

Heat Treatment

According to the invention, the freeze-dried product (contained in respective vials at the end of the freeze-drying process) advantageously undergoes an additional final step of heat treatment (or thermal treatment).

As mentioned before, the thermal treatment is preferably performed on the freeze-dried product in the sealed vials already containing the physiologically acceptable gas; alternatively, it can be performed on the freeze-dried product in the vials before filling them with the gas and sealing. In the first case the thermal treatment can be either accomplished within the freeze-drier apparatus or preferably in a separate heating device (e.g. an oven). In the second case the heating step is preferably performed within the lyophilizing apparatus; afterward, the atmosphere is saturated with the desired gas and the vials are sealed.

As observed by the Applicant, said heat treatment of the freeze-dried product surprisingly results in improved characteristics of the suspension of gas-filled microvesicles obtained upon reconstituting of the freeze-dried product, with respect to suspensions obtained from freeze-dried products which do not undergo such heat treatment.

Applicant observed in particular that such treatment results in an increased resistance to pressure of the obtained microvesicles.

The freeze-dried product is preferably heated at a temperature higher than 35° C. (e.g. 36° C.), more preferably at a temperature of 38° C. or higher. The maximum temperature of the heat treatment generally depends on the materials comprised in the freeze-dried product. For instance, such temperature shall be lower than the melting point of the material used as freeze-drying additive, which is the component forming most of the mass of the freeze-dried product (typically from 50 up to more than 600 times the weight of the active components forming the stabilizing layer of the microvesicles). For instance, PEG4000 has a melting temperature of 53-58° C. According to an embodiment, the heating temperature is preferably of 50° C. or lower. Preferred temperatures for the heat treatment are from 38° C. to 45° C.

The duration of the heat treatment generally depends on the temperature of the treatment; typically, the higher the temperature, the shorter the duration of the heating. As the materials forming the gas-filled microvesicles envelope (phospholipids in particular) may undergo degradation reaction if subjected to excessive temperatures for a too long period of time (with possible negative consequences on the characteristics of the reconstituted microvesicles), the duration of the heat treatment shall not be unnecessarily prolonged. While a treatment duration of about 8 hours may be sufficient (particularly in combination with temperatures higher than 45° C., e.g. 48° C.), the duration of the heat treatment is preferably performed for 12 hours, up to e.g. 20 hours, more preferably 14 to 18 hours. While in particular cases longer durations may well be applied (particularly in combination with temperatures lower than 45° C., preferably lower than 42° C.), the Applicant has observed that the characteristics of the final gas-filled microvesicles are only slightly if not at all further improved; such increased duration is thus in most cases not necessary and generally inconvenient in terms of manufacturing economy at the industrial scale.

In certain embodiments, the freeze-dried product comprises a mixture of a phospholipid and of a fatty acid, as above defined, in admixture with a freeze-drying protecting component. The thermal treatment of the invention has been proven to be particularly effective for improving the characteristics of gas-filled microvesicles comprising such mixture of components.

According to an embodiment, the freeze-dried product comprises DSPC, DPPG and palmitic acid in combination with a freeze-drying protecting component (e.g. polyetheleneglycol, such as PEG4000). Said freeze-dried product is preferably heated at a temperature of from about 40° C. to 48° C., particularly of about 45° C. (+/−3° C.) for at least eight hours, preferably for about 18 h (+/−4 h).

According to another embodiment of the invention, the freeze-dried product comprises DSPC, DPPE-PEG5000 and palmitic acid in combination with a freeze-drying protecting component (e.g. polyetheleneglycol, such as PEG4000). Said freeze-dried product is heated at a temperature of from about 36° C. to 45° C., particularly of about 39° C. (+/−3° C.) for at least eight hours, preferably for about 15 h (+/−5 h).

According to a further embodiment, said mixture of DSPC, DPPE-PEG5000 and palmitic acid further comprises a targeting lipopeptide, e.g. as described in WO2007/067979.

As mentioned above, the thermal treatment of the freeze-dried product according to the invention results in an increased resistance of the gas-filled microvesicles to pressure. Advantageously, microvesicles with increased resistance to pressure generally show an increased time persistency in the blood stream once injected.

Resistance to pressure of gas-filled microvesicles can be assessed by determining the empiric parameter "Pc50" or "critical pressure".

As explained in detail in the experimental part, the Pc50 of a suspension of gas-filled microvesicles identifies the value of applied overpressure (with respect to atmospheric pressure) at which the absorbance of a suspension of microvesicles drops to half of the absorbance of the suspension measured at atmospheric pressure, said applied overpressure resulting in a substantial reduction of the population of microvesicles with respect to the initial one (at atmospheric pressure). As a matter of fact, reduction of the absorbance of a suspension of microvesicles is related to the reduction of the initial population of gas-filled microvesicles, whereby the initially milky suspension (high concentration of microvesicles) becomes more and more transparent under increasing pressure (reduced concentration due to collapse of microvesicles). The higher the Pc50 values, the higher the resistance to pressure of microvesicles. For ultrasound diagnostic applications, a minimum Pc50 value of at least 12 kPa is desirable for gas-filled microvesicles, preferably at least 13 kPa (about 100 mmHg), more preferably at least 14 kPa (105 mmHg). For ultrasound therapeutic applications, generally needing longer persistency time in the blood flow, a minimum Pc50 value of at least 55 kPa (about 412 mmHg) is desirable, preferably at least 70 kPa (about 525 mmHg), more preferably at least 80 kPa (about 600 mmHg), while higher values of Pc50 are even more preferred.

Typically, the thermal treatment of the freeze-dried product according to the invention allows increasing the Pc50 of the reconstituted suspension of microvesicles of at least 5 kPa, preferably at least 8 kPa and more preferably at least 10 kPa with respect to the Pc50 of a reconstituted suspension obtained from a freeze-dried product which has not been submitted to such thermal treatment. Such increase of Pc50 may be up to 15 kPa and in some embodiments up to 25 kPa.

According to an embodiment (e.g. when the freeze-dried product comprises DSPC, DPPG, palmitic acid and PEG4000) a suspension of microvesicles reconstituted from freeze-dried product subjected to a thermal treatment according to the invention has a value of Pc50 of at least 20 kPa, preferably at least 22 kPa and more preferably of at least 25 kPa.

According to another embodiment (e.g. when the freeze-dried product comprises DSPC, DPPE-PEG5000 and palmitic acid in combination with a freeze-drying protecting component, e.g. polyetheleneglycol, such as PEG4000) a suspension of microvesicles reconstituted from a freeze-dried product subjected to a thermal treatment according to the invention has a value of Pc50 of at least at least 75 kPa, preferably at least 80 kPa and more preferably of at least 90 kPa.

Pharmaceutical Kit, Administration and Methods of Use

The vials containing the freeze-dried product can be advantageously packaged in a two component diagnostic and/or therapeutic kit, preferably for administration by injection. The kit preferably comprises the vial containing the freeze-dried product and a second container (e.g. a syringe barrel) containing the physiologically acceptable aqueous carrier for reconstitution.

The microvesicles of the present invention may be used in a variety of diagnostic and/or therapeutic techniques, including in particular ultrasound.

An aspect of the invention thus relates to the use in a method of diagnosing of a suspension of microvesicles reconstituted from freeze-dried product subjected to a thermal treatment according to the invention.

Diagnostic methods include any method where the use of the gas-filled microvesicles allows enhancing the visualisation of a portion or of a part of an animal (including humans) body, including imaging for preclinical and clinical research purposes. A variety of imaging techniques may be employed in ultrasound applications, for example including fundamental and harmonic B-mode imaging, pulse or phase inversion imaging and fundamental and harmonic Doppler imaging; if desired three-dimensional imaging techniques may be used.

Microvesicles according to the invention may typically be administered in a concentration of from about 0.01 to about 1.0 μL of gas per kg of patient, depending e.g. on their respective composition, the tissue or organ to be imaged and/or the chosen imaging technique. This general concentration range may of course vary depending on specific imaging applications, e.g. when signals can be observed at very low doses such as in colour Doppler or power pulse inversion.

In an embodiment said method of diagnosing comprises
 (i) administering to a patient a suspension of gas-filled microvesicles obtained by reconstitution of a freeze-dried product obtained according to the process of the invention; and
 (ii) detecting an ultrasound signal from a region of interest in said patient.

According to an embodiment, said suspension of gas-filled microvesicles comprises DSPC, DPPG, palmitic acid and PEG4000.

Reconstitution of the freeze-dried product is preferably made by dispersing it into a physiologically acceptable aqueous carrier, e.g. saline, in the presence of a physiologically acceptable gas, e.g $SF_6$, under gentle agitation.

Said suspension of microvesicles has preferably a value of Pc50 of at least 20 kPa, more preferably at least 22 kPa and even more preferably of at least 25 kPa.

In an embodiment, said method of diagnosing comprises ultrasound imaging of the heart, in particular to opacify the left ventricular chamber and to improve the delineation of the left ventricular endocardial border in adult patients with suboptimal echocardiograms.

In another embodiment, said method of diagnosing comprises ultrasound imaging of the liver, in particular for characterization of focal liver lesions in adult and pediatric patients.

In a further embodiment, said method of diagnosing comprises ultrasound imaging of the urinary tract, particularly for the evaluation of suspected or known vesicoureteral reflux in pediatric patients.

In another embodiment of said diagnostic method, said suspension of gas-filled microvesicles comprise DSPC, DPPE-PEG5000, palmitic acid, optionally a targeting lipopeptide and PEG4000. Preferably the targeting lipopeptide is a VEGF/KDR targeting lipopeptide, e.g. as described in WO2007/067979.

Possible other diagnostic imaging applications include scintigraphy, light imaging, and X-ray imaging, including X-ray phase contrast imaging.

Another aspect of the invention relates to the use in a method of therapeutic treatment of a suspension of microvesicles reconstituted from freeze-dried product subjected to a thermal treatment according to the invention.

Therapeutic techniques include any method of treatment (as above defined) of a patient which comprises the combined use of ultrasounds and gas-filled microvesicles either as such (e.g. in ultrasound mediated thrombolysis, high intensity focused ultrasound ablation, blood-brain barrier permeabilization, immunomodulation, neuromudulation, radiosensitization) or in combination with a therapeutic agent (i.e. ultrasound mediated delivery, e.g. for the delivery of a drug or bioactive compound to a selected site or tissue, such as in tumor treatment, gene therapy, infectious diseases therapy, metabolic diseases therapy, chronic diseases therapy, degenerative diseases therapy, inflammatory diseases therapy, immunologic or autoimmune diseases therapy or in the use as vaccine), whereby the presence of the gas-filled microvesicles may provide a therapeutic effect itself or is capable of enhancing the therapeutic effects of the applied ultrasounds, e.g. by exerting or being responsible to exert a biological effect in vitro and/or in vivo, either by itself or upon specific activation by various physical methods (including e.g. ultrasound mediated delivery).

Microvesicles according to the invention can typically be administered for therapeutic purposes in a concentration of from about 0.01 to about 5.0 µL of gas per kg of patient, depending e.g. from their respective composition, the type of subject under treatment, the tissue or organ to be treated and/or the therapeutic method applied.

In an embodiment said method of ultrasound therapeutic treatment comprises:
(i) administering to a patient a suspension of gas-filled microvesicles obtained by reconstitution of a freeze-dried product obtained according to the process of the invention;
(ii) identifying a region of interest in said patient to be submitted to a therapeutic treatment, said region of interest comprising said suspension of gas-filled microvesicles; and
(iii) applying an ultrasound beam for therapeutically treating said region of interest;
whereby said ultrasound therapeutic treatment is enhanced by the presence of said suspension of gas-filled microvesicles in said region of interest.

In an embodiment, said suspension of gas-filled microvesicles comprises DSPC, DPPE-PEG5000, palmitic acid, optionally a targeting lipopeptide and PEG4000.

Reconstitution of the freeze-dried product is preferably made by dispersing it into a physiologically acceptable aqueous carrier, e.g. saline, in the presence of a physiologically acceptable gas, e.g. a mixture of $C_4F_{10}$ and nitrogen, under gentle agitation.

Said suspension of microvesicles has preferably a value of Pc50 of at least 84 kPa, more preferably at least 88 kPa and even more preferably of at least 90 kPa, up to about e.g. 105 kPa.

In a further embodiment, the suspension of gas-filled microvesicles of the invention may be advantageously used in a method for separating cells, typically by buoyancy (also known as buoyancy-activated cell sorting, "BACS"). The method can be useful for separating a desired type of cells from other cells in a physiological liquid (e.g. blood or plasma). In an embodiment, the separation method comprises labelling a desired cell to be separated with a suitable labelled antibody capable of binding to a specific (and selective) receptor on said cell. The microvesicles of the invention are then added to the suspension of cells to be separated (including those bearing the labelled antibody); once admixed to the suspension of cells, the microvesicles associate through the ligand with the labelling residue bound to antibody/cell construct thus allowing separation of the cells by buoyancy (see e.g. WO 2017/117349). For instance, the labelled antibody is a biotinylated antibody, where the biotin residue is capable of associating with a respective moiety, such as for instance an avidin, neutravidin or streptavidin residue on a gas-filled microvesicles. The improved resistance to pressure allows using the microvesicles of the invention in a wide variety of methods for separating cells.

The following examples will help to further illustrate the invention.

EXAMPLES

Materials
DSPC: 1,2-distearoyl-sn-glycero-3-phosphocholine
DPPG-Na: 1,2-dipalmitoyl-sn-glycero-3-phospho-(1'-rac-glycerol) (sodium salt)
DPPE-PEG5000: 1,2-dipalmitoyl-sn-glycero-3-phospho-ethanolamine-N-[methoxy(polyethylene glycol)-5000] (ammonium salt)
PEG4000=Polyethylenglycol (MW=4000 g/mol)

Measurement of Pressure Resistance (Pc50)

The resistance to pressure of gas-filled microvesicles was evaluated using an in-house developed pressure nephelometer. Briefly, the microvesicles suspension was introduced into a spectrophotometer sample cell (airtight and connected to a pressurization system). The optical density (absorbance at 700 nm) of the suspension is continuously recorded while linearly increasing the pressure applied to the sample in the cell from atmospheric pressure (760 mmHg, 101.3 kPa,) to an over pressure of two bars (2280 mmHg, 303.9 kPa), at a rate of about 4 mmHg/s (533 Pa/s).

The Pc50 parameter ("critical pressure") characterizing each suspension identifies the overpressure (with respect to atmospheric pressure) at which the absorbance of the microvesicles suspension drops to half of its initial value.

Example 1

Preparation of Freeze-Dried Product (Batches 1a-1b)

The procedure illustrated in the working examples of WO 94/09829 was used for preparing two different batches (1a-1b) each consisting of several vials containing the freeze-dried product.

Briefly, DSPC, DPPG-Na and palmitic acid in a weight ratio of 4.75/4.75/1 were first dissolved in hexane/ethanol (8/2, v/v) at a concentration of about 5 g/L and the solvents were evaporated under vacuum. The solid residue was admixed with PEG4000 in a weight ratio of about 0.017:1, the mixture was dissolved in tert-butanol at around 60° C. and the clear solution was used to fill respective DIN8R vials (with a corresponding volume containing about 25 mg of the mixture). The vials were then rapidly cooled at −45° C. and then subjected the vacuum for removing the frozen solvent by sublimation. The temperature was then raised (above room temperature, not higher than 35° C.) and the remaining solvent was evaporated, down to a final amount of less than 0.5% by weight. At the end of the freeze-drying process, the ambient of the freeze-dryer was saturated with $SF_6$ at atmospheric pressure and the vials (containing the solid freeze-dried product in contact with $SF_6$) were stoppered and sealed.

The two batches were used for the subsequent heat treatment experiments.

Example 2

Preparation of Freeze-Dried Product (2a-2h)

The procedure illustrated in the working examples of WO2004/069284 was used for preparing eight different batches (2a-2h) each consisting of several vials containing the freeze-dried product.

Briefly, an emulsion of cyclooctane and water (about 1.5/100 v/v) containing about 90 mg/l of DSPC, 7 mg/l of palmitic acid, 60 mg/l of DPPE-PEG5000 and 100 g/l of PEG4000 is prepared (Megatron MT3000, Kinematica; 10'000 rpm) and sampled into DIN8R vials (about 1 ml/vial).

The vials were cooled at −50° C. under vacuum and then subjected to lyophilization, followed by secondary drying above room temperature until complete removal of water and solvent (less than 0.5% by weight), as described in example 1. At the end of the freeze-drying process, the headspace of the vials is saturated with a 35/65 mixture of $C_4F_{10}/N_2$ and the vials are stoppered and sealed.

The different batches (1a to 1h) were used for the subsequent heat treatment experiments.

Example 3

Effect of the Heat Treatment on Batches Manufactured According to Example 1

The vials of the various batches prepared according to examples 1 were submitted to different heat treatments and the effect on the characteristics of the reconstituted suspensions of gas-filled microvesicles were observed.

Experiment 3.1

The vials of batch 1a were submitted to a heating temperature of 48° C. for a time ranging from 8 hours to one week (five vials for each group). The product in the vial was then reconstituted with 5 ml of saline and the characteristics of the microvesicles in the suspension were measured. Results are reported in the following table 1.

TABLE 1

| Batch 1a | |
| --- | --- |
| Heating time 48° C. | Pc50 (kPa) mean value |
| No heating | 14.4 |
| 8 hours | 24.8 |
| 16 hours | 25.5 |
| 24 hours | 28.7 |
| 48 hours | 28.8 |
| One week | 32.0 |

As inferable from the above results, a substantial increase in the pressure resistance can be observed after 8 hours of heat treatment, with respect to the untreated freeze-dried samples. Such pressure resistance slightly increases in time, up to a maximum after one week of treatment. However, as observed by the Applicant, a too long heating time (e.g. after 24 hours and particularly above 48 hours) may negatively impact on other characteristics of the gas-filled microvesicles, such as their total number, the total volume of gas and/or their mean size.

Experiment 3.2

In a second experiment, the vials of batch 1b were heated at temperatures of 40° C., 45° C. and 49° C. for time periods of 12, 16 or 20 hours (three vials for each group, for a total of 27 vials). The product in the vial was then reconstituted with 5 ml of saline and the characteristics of the microvesicles in the suspension were measured. Results are reported in the following table 2.

TABLE 2

| Batch 1b | | |
| --- | --- | --- |
| Heating time | T (° C.) | Pc50 (kPa) mean value |
| 12 hours | 40 | 22.8 |
| 16 hours | 40 | 23.6 |
| 20 hours | 40 | 23.7 |
| 12 hours | 45 | 25.5 |

TABLE 2-continued

| Batch 1b | | |
| --- | --- | --- |
| Heating time | T (° C.) | Pc50 (kPa) mean value |
| 16 hours | 45 | 22.5 |
| 20 hours | 45 | 22.4 |
| 12 hours | 49 | 24.1 |
| 16 hours | 49 | 24.4 |
| 20 hours | 49 | 24.9 |

As inferable from the above data, a substantial increase in the pressure resistance is obtained with the heat treatment of the freeze-dried products (with respect to the initial value of about 14 kPa). While a higher increase of Pc50 may generally be observed for treatments at 49° C., treating at this temperature may however negatively impact on other characteristics of the reconstituted gas-filled microvesicles, particularly on the mean size values.

Example 4

Effect of the Heat Treatment on Batches Manufactured According to Example 2

The vials of the various batches (2a-2h) prepared according to example 2 were submitted to different heat treatments and the effect on the characteristics of the reconstituted suspensions of gas-filled microvesicles were observed.

Experiment 4.1

The vials of batch 2a were submitted to a heating temperature of 40° C. or 45° C. for 16 hours or not heated. The product in the vial was then reconstituted with 5 ml of saline and the characteristics of the microvesicles in the suspension were measured. Results are reported in the following table 3.

TABLE 3

| Batch 1a | |
| --- | --- |
| Heating T for 16 h | Pc50 (kPa) mean value |
| No heating | 66.1 |
| 40° C. | 84.8 |
| 45° C. | 78.8 |

As inferable from the above data, a substantial increase in the pressure resistance is obtained upon heat treatment also for batches manufactured according to the procedure of example 2.

Experiment 4.2

The vials of batch 2b were submitted to a heating temperature of 40° C. for a time ranging from 16 to 88 hours, or not heated. The product in the vial was then reconstituted with 5 ml of saline and the characteristics of the microvesicles in the suspension were measured. Results are reported in the following table 4.

TABLE 4

| Batch 2b | |
| --- | --- |
| Heating time T = 40° C. | Pc50 (kPa) mean value |
| No heating | 82.1 |
| 16 hours | 99.0 |
| 40 hours | 103.6 |

TABLE 4-continued

Batch 2b

| Heating time T = 40° C. | Pc50 (kPa) mean value |
|---|---|
| 64 hours | 98.6 |
| 88 hours | 102.5 |

As inferable from the above data, a substantial increase in the pressure resistance is obtained upon heat treatment at 40° C. A duration of the treatment of 16 h is generally considered sufficient, also for avoiding possible negative effects caused by longer thermal treatments on other characteristics of the microvesicles (e.g. increase of large size microvesicles in the reconstituted suspension).

Experiment 4.3

The vials of batches 2c-2g were submitted to a heating temperature of 40° C. for a period of 16 hours, or not heated. The product in the vial was then reconstituted with 5 ml of saline and the characteristics of the microvesicles in the suspension were measured. Results are reported in the following table 5.

TABLE 5

Batches 2c-2g (40° C., 16 h)

| Batch No. | Thermal Treatment | Pc50 (kPa) mean value |
|---|---|---|
| 2c | No | 70.6 |
| 2c | Yes | 93.7 |
| 2d | No | 74.1 |
| 2d | Yes | 94.3 |
| 2e | No | 69.6 |
| 2e | Yes | 94.2 |
| 2f | No | 62.8 |
| 2f | Yes | 79.8 |
| 2g | No | 55.4 |
| 2g | Yes | 81.3 |

As inferable from the above table, for the suspensions of microvesicles reconstituted from the various batches an increase in pressure resistance of more than 15 kPa or more and up to about 25 kPa is obtained after heat treatment of the freeze-dried products.

Experiment 4.4

The vials of batch 2h were submitted to a heat treatment at 38° C. for a time ranging from two to 24 hours. The product in the vial was then reconstituted with 5 ml of saline and the characteristics of the microvesicles in the suspension were measured. Results are reported in the following table 6.

TABLE 6

Batch 2h

| Heating time (h) at 38° C. | Pc50 (kPa) mean value |
|---|---|
| 0 | 63.19 |
| 2 | 73.33 |
| 4 | 74.66 |
| 6 | 79.33 |
| 8 | 80.26 |
| 12 | 82.66 |
| 16 | 79.73 |
| 24 | 83.06 |

As inferable from the above table, an increasing pressure resistance of the microvesicles in the reconstituted suspension is obtained upon heating the freeze-dried material for an increasing time, up to 8-12 hours at 38° C. Further heating of the material (16 or 24 hours) does not substantially further increase the pressure resistance.

The invention claimed is:

1. A method of manufacturing a freeze-dried composition suitable for the preparation of a suspension of stabilized gas-filled microbubbles, said composition comprising: (i) an amphiphilic material comprising a phospholipid and a fatty acid; and (ii) a polyethylene glycol as freeze-drying protecting component; which comprises:
   a. preparing a liquid mixture comprising said amphiphilic material and said freeze-drying protecting component in a solvent;
   b. freeze-drying the liquid mixture to remove said solvent and obtain a freeze-dried product; and
   c. after completion of the freeze-drying of step b, heating said freeze-dried product at ambient pressure at a temperature higher than 35° C. and lower than the melting point of the polyethylene glycol freeze-drying protecting component, for a period of time of from eight to twenty hours, wherein the freeze-dried product of step b has not been reconstituted prior to step c.

2. The method according to claim 1 wherein said liquid mixture comprises said amphiphilic material and said freeze-drying protecting component dispersed in an organic solvent.

3. The method according to claim 1 wherein said liquid mixture comprises said amphiphilic material and said freeze-drying protecting component dispersed in an aqueous emulsion of a water immiscible solvent and water.

4. The method according to claim 1 wherein said heating step is carried out at a temperature of from 38° C. to the melting point of the polyethylene glycol freeze-drying protecting component.

5. The method according to claim 1 wherein said heating step is carried out at a temperature of from 40° C. to the melting point of the polyethylene glycol freeze-drying protecting component.

6. The method according to claim 1 wherein said phospholipid comprises dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2 Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC), 1-palmitoyl-2-oleylphosphatidylcholine (POPC), 1-oleyl-2-palmitoyl-phosphatidylcholine (OPPC), dilauroyl-phosphatidylglycerol (DLPG) and its alkali metal salts, diarachidoylphosphatidyl-glycerol (DAPG) and its alkali metal salts, dimyristoylphosphatidylglycerol (DMPG) and its alkali metal salts, dipalmitoylphosphatidylglycerol (DPPG) and its alkali metal salts, distearoylphosphatidylglycerol (DSPG) and its alkali metal salts, dioleoyl-phosphatidylglycerol (DOPG) and its alkali metal salts, dimyristoyl phosphatidic acid (DMPA) and its alkali metal salts, dipalmitoyl phosphatidic acid (DPPA) and its alkali metal salts, distearoyl phosphatidic acid (DSPA), diarachidoylphosphatidic acid (DAPA) and its alkali metal salts, dimyristoyl-phosphatidylethanolamine (DMPE), dipalmitoylphosphatidylethanolamine (DPPE), distearoyl phosphatidyl-ethanolamine (DSPE), dioleylphosphatidyl-ethanolamine (DOPE), diarachidoylphosphatidylethanolamine (DAPE), dilinoleylphosphatidylethanolamine (DLPE), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and di stearoyl sphingomyelin (DSSP), dilauroyl-phosphatidylinositol (DLPI), diarachidoylphosphatidylinositol (DAPI), dimyristoylphosphatidylinositol (DMPI), dipalmitoylphosphatidylinositol (DPPI), distearoylphosphatidylinositol (DSPI) or dioleoylphosphatidylinositol (DOPI).

7. The method according to claim 1 wherein said fatty acid comprises capric (n-decanoic), lauric (n-dodecanoic), myristic (n-tetradecanoic), palmitic (n-hexadecanoic), stearic (n-octadecanoic), arachidic (n-eicosanoic), behenic (n-docosanoic) or n-tetracosanoic acid.

8. The method according to claim 1, wherein said amphiphilic material comprises DSPC, DPPG and palmitic acid.

9. The method according to claim 1, wherein said amphiphilic material comprises DSPC, DPPE-PEG5000 and palmitic acid.

10. The method according to claim 8, wherein said heating step is carried out at a temperature of from 40° C. to 48° C.

11. The method according to claim 9, wherein said heating step is carried out at a temperature of from 36° C. to 45° C.

12. The method according to claim 1, wherein said heating in step c is performed for a period of time of from twelve to twenty hours.

13. The method according to claim 1 wherein said liquid mixture is sampled into glass vials which are loaded into a freeze-dryer.

14. The method according to claim 13 which comprises, at the completion of step b, saturating the headspace of the vials containing the freeze-dried product with a physiologically acceptable gas and then stoppering and sealing the vials.

15. A method of manufacturing a suspension of gas-filled microvesicles comprising
  (i) preparing a liquid mixture comprising an amphiphilic material and a freeze-drying protecting component in a solvent, wherein the amphiphilic material comprises a phospholipid and a fatty acid and the freeze-drying protecting component is a polyethylene glycol;
  (ii) freeze-drying the liquid mixture to remove said solvent and obtain a freeze-dried product;
  (iii) after completion of the freeze-drying of step (ii), heating said freeze-dried product at ambient pressure at a temperature higher than 35° C. and lower than the melting point of the polyethylene glycol freeze-drying protecting component, for a period of time from eight to twenty hours, wherein the freeze-dried product of step (ii) has not been reconstituted prior to step (iii); and
  (iv) reconstituting said freeze-dried product with a pharmaceutically acceptable liquid carrier in the presence of a physiologically acceptable gas under gentle agitation to obtain a suspension of gas-filled microvesicles.

16. The method of claim 15, wherein the physiologically acceptable gas is selected from $SF_6$, $C_3F_8$, and $C_4F_{10}$, optionally in admixture with air or nitrogen.

17. The method of claim 15, wherein the phospholipid consists of the combination of DSPC and the sodium salt of DPPG, and the fatty acid consists of palmitic acid.

18. The method of claim 15, wherein the phospholipid consists of the combination of DSPC and DPPE-PEG5000 and the fatty acid consists of palmitic acid.

19. A method comprising:
  (i) preparing a liquid mixture comprising an amphiphilic material and a freeze-drying protecting component in a solvent, wherein the amphiphilic material comprises a phospholipid and a fatty acid; and the freeze-drying protecting component is a polyethylene glycol;
  (ii) freeze-drying the liquid mixture to remove said solvent and obtain a freeze-dried product;
  (iii) after completion of the freeze-drying of step (ii), heating said freeze-dried product at ambient pressure at a temperature higher than 35° C. and lower than the melting point of the polyethylene glycol freeze-drying protecting component, for a period of time from eight to twenty hours, wherein the freeze-dried product of step (ii) has not been reconstituted prior to step (iii); and
  (iv) reconstituting said freeze-dried product with a pharmaceutically acceptable liquid carrier in the presence of a physiologically acceptable gas under gentle agitation in order to obtain a suspension of gas-filled microvesicles;
  (v) administering to a patient said suspension of gas-filled microvesicles; and
  (vi) detecting an ultrasound signal from a region of interest in said patient.

20. The method according to claim 19, wherein the region of interest in said patient is the heart.

21. The method according to claim 19, wherein the region of interest in said patient is the liver.

22. The method according to claim 19, wherein the region of interest in said patient is the urinary tract.

23. The method of claim 19, wherein the physiologically acceptable gas is selected from $SF_6$, $C_3F_8$, and $C_4F_{10}$, optionally in admixture with air or nitrogen.

24. The method of claim 19, wherein the phospholipid consists of the combination of DSPC and the sodium salt of DPPG, and the fatty acid consists of palmitic acid.

25. The method of claim 19, wherein the phospholipid consists of the combination of DSPC and DPPE-PEG5000 and the fatty acid consists of palmitic acid.

* * * * *